(12) United States Patent
Maltese et al.

(10) Patent No.: US 11,602,531 B2
(45) Date of Patent: Mar. 14, 2023

(54) VACUOLE-INDUCING COMPOUNDS, METHODS OF MAKING AND USING THE SAME

(71) Applicant: The University of Toledo, Toledo, OH (US)

(72) Inventors: William A. Maltese, Toledo, OH (US); Zehui Li, Toledo, OH (US); Christopher J. Trabbic, Toledo, OH (US); Paul W. Erhardt, Toledo, OH (US)

(73) Assignee: The University of Toledo, Toledo, OH (US)

( * ) Notice: Subject to any disclaimer, the term of this patent is extended or adjusted under 35 U.S.C. 154(b) by 338 days.

(21) Appl. No.: 17/075,065

(22) Filed: Oct. 20, 2020

(65) Prior Publication Data

US 2021/0038586 A1 Feb. 11, 2021

Related U.S. Application Data

(63) Continuation of application No. 16/484,648, filed as application No. PCT/US2018/016108 on Jan. 31, 2018, now abandoned.

(60) Provisional application No. 62/458,660, filed on Feb. 14, 2017.

(51) Int. Cl.
| | | |
|---|---|---|
| *A61K 31/4439* | (2006.01) | |
| *C12N 5/00* | (2006.01) | |
| *C12N 1/38* | (2006.01) | |
| *A61K 31/53* | (2006.01) | |
| *A61K 31/5377* | (2006.01) | |

(52) U.S. Cl.
CPC .......... *A61K 31/4439* (2013.01); *A61K 31/53* (2013.01); *A61K 31/5377* (2013.01); *C12N 1/38* (2013.01); *C12N 5/0006* (2013.01); *C12N 2500/30* (2013.01); *C12N 2501/06* (2013.01)

(58) Field of Classification Search
CPC .... A61K 31/4439; C12N 1/38; C12N 5/0006; C12N 2500/30; C12N 2501/06
See application file for complete search history.

*Primary Examiner* — Theodore R. Howell
(74) *Attorney, Agent, or Firm* — MacMillan, Sobanski & Todd, LLC (57) ABSTRACT

Vacuole- or exosome-inducing indole-based chalcone and substituted triazole-hydrazone compounds that induce endosomal vacuolization and increase exosome yield, but do not trigger growth arrest or cell death, and methods of making and using are described.

9 Claims, 9 Drawing Sheets

VACUOLE-INDUCING COMPOUNDS, METHODS OF MAKING AND USING THE SAME

CROSS-REFERENCE TO RELATED APPLICATIONS

This application is a continuation of Ser. No. 16/484,648 filed Aug. 8, 2019, which is a national stage application filed under 35 USC § 371 of international application PCT/US2018/016108 filed Jan. 31, 2018, which claims the benefit of U.S. Ser. No. 62/458,660 filed Feb. 14, 2017, the entire disclosure of which is expressly incorporated herein by reference.

STATEMENT REGARDING FEDERALLY SPONSORED RESEARCH

The invention was made with U.S. Government support under grant number R01 CA115495 awarded by the National Institutes of Health. The United States Government has certain rights in the invention.

BACKGROUND OF THE INVENTION

Exosomes are vesicles with diameters in the range of 30-120 nm, which are released from many types of cells. Exosomes originate as intralumenal vesicles (ILVs) within multivesicular late endosomes (MVEs). The vesicles are released into the extracellular environment upon fusion of MVEs with the plasma membrane. MVEs are commonly viewed as occupying an intermediate position between early endosomes and lysosomes in the endolysosomal degradative pathway of eukaryotic cells. Several distinct multiprotein ESCRTs (endosomal sorting complexes required for transport) function in MVE biogenesis. Proteins displaying monoubiquitin signals interact with the ESCRTs and are sorted into the intralumenal vesicles, which are ultimately degraded when the MVEs merge with lysosomes. While exosomes contain proteins typically found in ILVs, there is some evidence that they may be derived from functionally distinct subpopulations of MVEs that are routed to the plasma membrane instead of the lysosomes. The mechanisms that control the trafficking of MVEs to the cell surface and the release of exosomes are not well understood. Nevertheless, several common factors appear to influence this process, including ceramide levels, intracellular calcium, microenvironmental pH and specific Rab GTPases.

Despite intense interest in the potential diagnostic and therapeutic applications of exosomes, small molecules that can either inhibit or stimulate exosome production without affecting cell growth or viability are lacking. Many compounds that perturb endolysosomal vesicle trafficking and induce vacuolization of late endosomal compartments have been identified. However, little is known about the possible effects of such compounds on exosome biogenesis because many of them are cytotoxic.

It would be useful to have small molecules that can either inhibit or stimulate exosome production without affecting cell growth or viability.

SUMMARY OF THE INVENTION

Provided herein a method for increasing exosome production in a cell by exposing the cell to an indole-pyridinyl-propenone compound that induces endosomal vacuolization but does not trigger growth arrest or cell death.

In certain embodiments, the indole-pyridinyl-propenone compound has the following chemical structure:

where R=OH, OCH$_3$, OCH$_2$CH$_3$, OCH(CH$_3$)$_2$, NHCOCH$_3$ or NHCO$_2$C(CH$_3$)$_3$; and
R'=H, CH$_3$, CH$_2$CH$_2$CH$_3$, CH(CH$_3$)$_2$, or CH$_2$CH(CH$_3$)$_2$;
excluding where R=OCH$_3$ and R'=CH$_3$.

In certain embodiments, the indole-pyridinyl-propenone compound has the formula where: R=OCH$_3$; and, R'=H, CH$_2$CH$_2$CH$_3$, CH(CH$_3$)$_2$, or CH$_2$CH(CH$_3$)$_2$.

In certain embodiments, the indole-pyridinyl-propenone compound has the formula where: R=OCH$_3$, and R'=CH$_2$CH$_2$CH$_3$ (i.e., 3-(5-methoxy-2-propyl-1H-indol-3-yl)-1-(4-pyridinyl)-2-propen-1-one (MOPIPP).

In certain embodiments, the indole-pyridinyl-propenone compound has the formula where: R=OH, OCH$_2$CH$_3$, OCH(CH$_3$)$_2$, NHCOCH$_3$ or NHCO$_2$C(CH$_3$)$_3$; and, R'=CH$_3$.

In certain embodiments, the indole-pyridinyl-propenone compound has the formula where: R=OCH$_2$CH$_3$; and, R'=CH$_3$.

In certain embodiments, the indole-pyridinyl-propenone compound has the formula where: R=OCH$_2$CH$_3$; and R'=CH$_2$CH$_2$CH$_3$.

In another aspect, there is provided a method for increasing exosome production in a cell culture, comprising: exposing the culture to a substituted triazole-hydrazone compound that induces endosomal vacuolization but does not trigger cell death or attenuate cell growth.

In certain embodiments, such substituted triazole-hydrazone compound has the following chemical structure:

wherein R=CH$_2$, NH, O; and R'= an electron withdrawing group. Non-limiting examples of electron withdrawing groups include: halides (F, Cl, Br and I), trifluoromethyl (CF$_3$), nitro (NO$_2$), acetyl (—COCH$_3$) and trimethylammonium (N(CH$_3$)$_3$ wherein this becomes positively charged when further attached as a substituent. Also, in certain embodiments, the substituted triazole-hydrazone compound has the formula where R=O; and R'=Iodo.

Also described herein is a method where exosomes are collected exosomes by one or more of the following: ultracentrifugation; column chromatography; size exclusion; and filtration through a device containing an affinity matrix that is selective toward exosomes.

Also described is a method using such exosomes by harvesting the exosomes for use as nanocarriers for packaging and delivery of a therapeutic material to a subject in need thereof.

In certain embodiments, the therapeutic material comprises one or more of: small molecules, miRNAs, and proteins.

In certain embodiments, the cell comprises one or more of: multipotent mesenchymal stromal cells; stem cells; and, cancer cells. Further, in certain embodiments, the cell is a mammalian cell.

Also described herein is a method of producing transiently expressed miRNA containing cells, comprising: transfecting a cell population of cells capable of producing exosomes produced according to the method described herein with one or more plasmids encoding miRNA; harvesting cells from the cell population after transfection; and, confirming the presence of the miRNA in one or more of the harvested cells.

Also described herein is a method of treating a subject in need thereof with modified exosomes, comprising: transfecting exosome-producing cells produced by the method described herein, with one or more carriers encoding a therapeutic material; harvesting the exosomes from the cell population or media containing same after transfection; confirming the presence of the therapeutic material in one or more of the harvested exosomes; and, administering to the subject one or more of the harvested exosomes in a pharmaceutically effective amount to treat the subject.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

FIGS. 1A-1D—Comparison of cell and exosome morphologies in cultures treated with MOPIPP and vacuolin-1.

In FIG. 2C, representative blots are shown, and the fold-increase in the treated cells relative to the controls is graphed below each blot (mean±SEM). The cells from the same experiments (see FIG. 2A), were subjected to western blot analysis for the indicated proteins, with equal amounts of protein loaded on each lane (FIG. 2B and FIG. 2D). In FIG. 2D, representative blots are shown, with signals for the proteins in the treated cells expressed as percent of the corresponding DMSO controls in the graphs below each blot (mean±SEM).

FIGS. 3A-3D—MOPIPP or vacuolin-1 do not have major effects on the profile of miRNAs represented in exosomes.

DETAILED DESCRIPTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Definitions

In general, the terms and phrases used herein have their art-recognized meaning, which can be found by reference to texts, journal references and contexts known to those skilled in the art.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the invention, the preferred methods and materials are now described. Nothing herein is to be construed as an admission that the invention is not entitled to antedate such disclosure by virtue of prior invention.

Every formulation or combination of components described or exemplified herein can be used to practice the invention, unless otherwise stated.

When a group of substituents is disclosed herein, it is understood that all individual members of that group and all subgroups, including any isomers and enantiomers of the group members, are disclosed separately. When a Markush group or other grouping is used herein, all individual members of the group and all combinations and subcombinations possible of the group are intended to be individually included in the disclosure. It is intended that any one or more members of any Markush group or listing provided in the specification can be excluded from the invention if desired. When a compound is described herein such that a particular isomer or enantiomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Specific names of compounds are intended to be exemplary, as it is known that one of ordinary skill in the art can name the same compounds differently.

Every formulation or combination of components described or exemplified herein can be used to practice the invention, unless otherwise stated.

All publications mentioned herein are incorporated herein by reference for the purpose of describing and disclosing components that are described in the publications that might be used in connection with the presently described invention.

The definitions are provided to clarify their specific use in the context of the invention.

Additionally, described herein are pharmaceutically acceptable derivatives of the inventive compounds, and methods of treating a subject using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof.

The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

As used herein, the terms "patient" and "subject" are intended to include living organisms in which certain conditions as described herein can occur. Examples include humans, monkeys, cows, sheep, goats, dogs, cats, mice, rats, and transgenic species thereof. In a preferred embodiment, the patient is a primate. In an even more preferred embodiment, the primate is a human. Other examples of subjects include experimental animals such as mice, rats, dogs, guinea pigs, cats, goats, sheep, pigs, and cows. The experimental animal can be an animal model for a disorder, e.g., a transgenic mouse with cancer.

As used herein, the term "$IC_{50}$" refers to an inhibitory dose which is 50% of the maximum response obtained.

General Description

Various indolyl pyridinyl propenones are described in Maltese et al. U.S. Pat. No. 9,023,871 issued May 5, 2015; Maltese et al. U.S. Pat. No. 9,028,796 issued May 12, 2015; Maltese et al. U.S. Pat. No. 9,061,994 issued Jun. 23, 2015; Trabbic et al., "Differential Induction of Cytoplasmic Vacuolization and Methuosis by Novel 2-Indolyl-Substituted Pyridinylpropenones," ACS Med. Chem. Lett., 5 (2014) 73-77; and, Trabbic et al., "Synthesis and biological evaluation of indolyl-pyridinyl-propenones having either methuosis or microtubule disruption activity," J. Med. Chem., 58 (2015) 2489-2512, the entire contents of which are explicitly incorporated herein.

Various indolyl pyridinyl propenone compounds induce the formation of cytoplasmic vacuoles in cultured human cells without causing appreciable cytotoxicity or growth arrest.

Described herein are methods using the vacuole-inducing analogs of the indolyl pyridinyl propenone chemical family to stimulate an increase in exosome production in cultured cells without altering the cargo carried by these exosomes.

Also described herein are methods using the vacuole-inducing analogs of the indolyl pyridinyl propenone chemical family to stimulate an increase in exosome release by cultured cells without altering the cargo carried by these exosomes.

Also described herein are therapeutic applications using such exosomes; for example, using these exosomes as nanocarriers for packaging and delivery of a desired cargo to the cell. In certain embodiments, the cargo can include small molecules (e.g., anti-cancer drugs), miRNAs, and proteins.

These exosomes are useful in that they may incorporate various cargoes in producer cells.

The methods of production of these exosomes overcomes one of the major impediments to more widespread development of exosome-based therapies; that is, the low yield of exosomes.

For example, one compound 3-(5-methoxy-2-propyl-1H-indol-3-yl)-1-(4-pyridinyl)-2-propen-1-one (MOPIPP), and related molecules are useful as non-cytotoxic pharmacological agents to boost exosome production.

MOPIPP and related molecules are useful in enhancing large-scale commercial production of exosomes from cultured cells, particularly for therapeutic purposes.

The following examples show the use of cultured human glioblastoma cells to assess the effects of MOPIPP and vacuolin-1 on exosome production. The results show that both compounds may have utility as non-toxic agents to enhance the cellular release of exosomes.

EXAMPLES

The present invention is further defined in the following Examples, in which all parts and percentages are by weight and degrees are Celsius, unless otherwise stated. It should be understood that these Examples, while indicating preferred embodiments, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified.

It is to be understood, that throughout the specification and claims herein, the terms "vacuole," "vesicle" and "exosome" generally refer to a space within the cytoplasm of a cell, enclosed by a membrane and typically containing fluid, which may also be released from the cell. For example, exosomes are generally described as small vesicles created and released from the plasma membrane of various types of cells, especially immune cells, and capable of inducing antigen-specific immune responses.

Materials and Methods

Cell Culture

U251 human glioblastoma cells were purchased from the DCT Tumor Repository (National Cancer Institute, Frederick, Md.). Stock cultures were maintained in Dulbecco's modified Eagle medium (DMEM) containing 10% (v/v) fetal bovine serum (FBS) (JR Scientific, Woodland, Calif.) at 37° C. with an atmosphere of 5% $CO_2$ in air. Cultures were passaged for less than 6 months and were monitored periodically for *Mycoplasma* contamination.

Isolation of Exosomes

Prior to beginning studies, cells were seeded in 10 cm diameter culture dishes at 500,000 cells/dish and maintained for 24 h in DMEM supplemented with 10% Gibco™ exosome-depleted FBS (ThermoFisher Scientific, Waltham, Mass.). The medium was then replaced with fresh medium containing either 10 µM MOPIPP (synthesized as described in Trabbic et al., "Differential Induction of Cytoplasmic Vacuolization and Methuosis by Novel 2-Indolyl-Substituted Pyridinylpropenones, ACS Med. Chem. Lett., 5 (2014) 73-77) or 1 µM vacuolin-1 (Santa Cruz Biotechnology, Santa Cruz, Calif.) dissolved in DMSO. Control cultures contain an equivalent volume of the DMSO vehicle (0.1%) in the medium. After 24 h, the medium was collected from the dishes (typically 10-12 dishes per condition) and the attached cells were pooled and counted with a Coulter Counter (model Z1). Exosomes were isolated from medium using the Exo-Spin™ Exosome Purification system (Cell Guidance Systems, St. Louis, Mo.). The medium was precleared by centrifugation at 4° C., first at 300×g for 10 min and then at 16,000×g for 30 min. Then a volume of Buffer A equal to half the volume of medium was added and the mixture was incubated overnight at 4° C. The precipitate, enriched with exosomes, was collected by centrifugation at 16,000×g for 1 h, and the pellet was re-suspended in 1000 of Dulbecco's phosphate-buffered saline (PBS), pH 7.4. The material was applied to an Exo-Spin column equilibrated with PBS, and the purified exosomes were eluted in 200 µl of PBS.

Electron Microscopy

Aliquots of purified exosomes obtained from control and drug-treated cell cultures were fixed with 4% paraformaldehyde and stained with 2% uranyl acetate on Formvar carbon-coated electron microscopy grids. Vesicles were visualized using a Hitachi HD-2300 transmission electron microscope at an accelerating voltage of 200 kV. Electron microscopy of vacuolated cells was carried out (as described in Johnson et al. "Gene silencing reveals a specific function of hVps34 phosphatidylinositol 3-kinase in late versus early endosomes, J. Cell Sci., 119 (2006) 1219-1232).

Dynamic Light Scattering (DLS)

Exosomes suspended in PBS were subjected to DLS using a Nicomp 380 ZLS instrument (Particle Sizing Systems, Port Richey, Fla.). Samples were placed in the path of a helium neon laser of wavelength 658 nm at 23° C., and data were collected at a scattering angle of 90°. For each sample, three measurements of 8 min each were performed, and the particle size distribution (number-weighted diameter) was displayed.

Immunoblot Analysis

The cells in the dishes used for collection of exosomes were washed three times with PBS and lysed in SDS sample buffer (Laemmli, "Cleavage of structural proteins during the assembly of the head of bacteriophage T4, Nature, 227 (1970) 680-685). The protein concentration was determined by colorimetric assay using Bio-Rad reagent (Bio-Rad, Richmond, Calif.). Samples containing equal amounts of total cell protein were subjected to SDS-PAGE and immunoblot analysis (as described in Maltese et al., "Retention of the Alzheimer's amyloid precursor fragment C99 in the endoplasmic reticulum prevents formation of amyloid beta-peptide, J. Biol. Chem., 276 (2001) 20267-20279). For analysis of proteins in exosomes, equal volumes of purified exosomes isolated from control or treated cells were mixed with ⅕ volume of 5×SDS sample buffer prior to SDS-PAGE. Monoclonal antibodies against CD63 and LAMP-1 were obtained from the Developmental Studies Hybridoma Bank (Iowa City, Iowa). Antibodies against Alix and cytochrome c were from Santa Cruz Biotechnology (Santa Cruz, Calif.), and the antibody against Lamin $B_2$ was from Cell Signaling Technology (Danvers, Mass.). HRP-coupled goat anti-mouse IgG was from BD Biosciences (San Jose, Calif.). Chemiluminescent signals on the membranes were quantified using an Alpha Innotech FluorChem HD2 imaging system with Alpha View software.

Analysis of miRNAs

Total RNA was extracted and purified from cultured cells or exosomes using QIAzol™ lysis reagent followed by RNAeasy Mini spin-columns, according to the manufacturer's protocol (SA Biosciences/Qiagen, Germantown, Md.). For each sample, cDNA was generated by reverse transcription of 150 ng of total RNA, using the miScript II RT kit (Qiagen). RNA and cDNA were quantified and checked for purity (OD 260/280) using a Nano-Drop-1000 spectrophotometer (ThermoFisher). For initial profiling of the miRNAs expressed in control or MOPIPP-treated cells, equal amounts of cDNA were applied to Human Brain Cancer miScript® miRNA PCR arrays (MIHS-108Z) (SA Biosciences/Qiagen), and real-time PCR reactions were carried in an Applied Biosystems StepOne Plus™ system using SYBR Green master mix. Raw Ct values for the individual miRNAs were normalized to the average Ct value for six snoRNA/snRNA miScript PCR controls included on each array, yielding ΔCt values. For comparisons of the miRNA contents of exosomes collected from the medium of cells treated with MOPIPP, vacuolin-1 or vehicle (DMSO), individual miScript primers were purchased for six of the most highly expressed miRNAs detected in U251 cells (SA Biosciences/Qiagen). The primers were reconstituted in SYBR green master mix and combined with cDNAs derived from equal amounts of exosomal RNA (150 ng). RT-PCR reactions were carried out in triplicate to obtain Ct values for each miRNA.

Results

Characterization of Exosomes

Figure 1A:
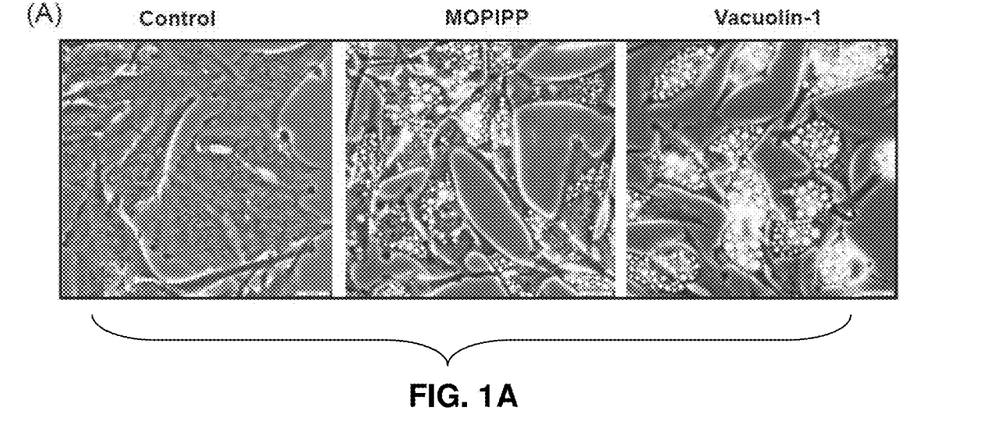
(FIG. 1A) U251 cells were examined by phase contrast microscopy after 24 h treatment with 10 μM MOPIPP, 1 μM vacuolin-1 or an equivalent volume of DMSO (control). Scale bars=20 μm.
Figure 1B:
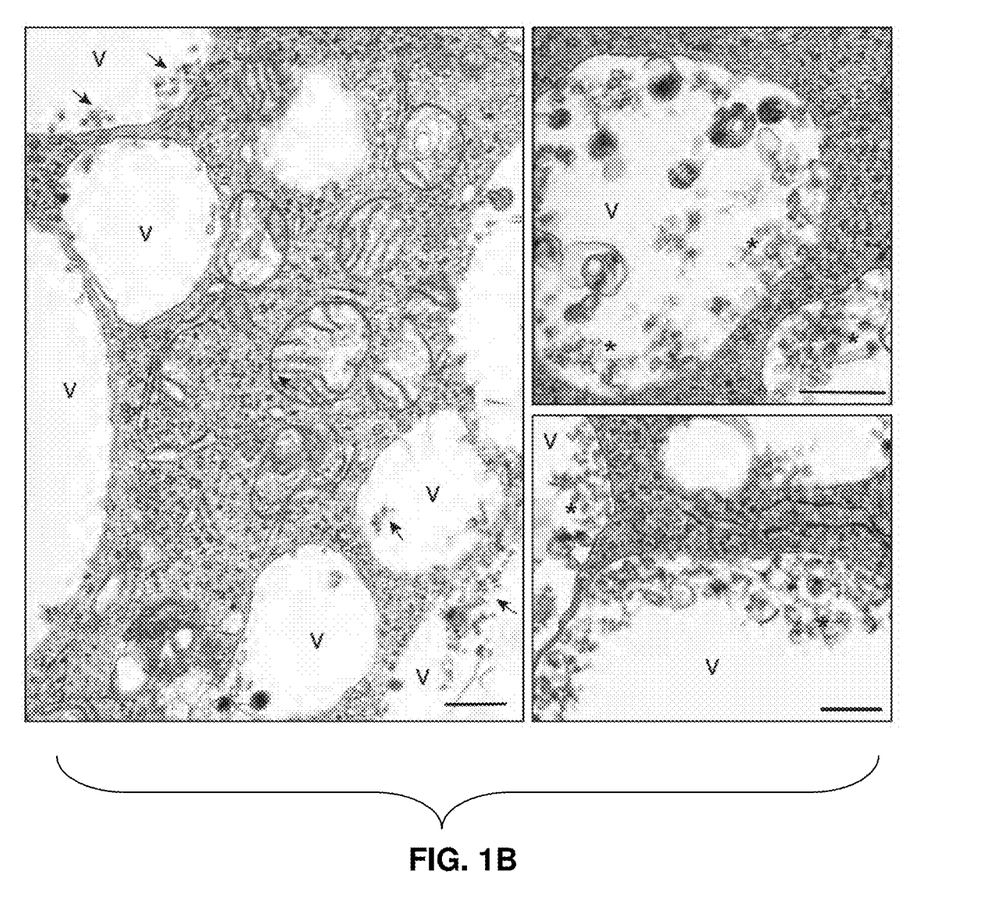
(FIG. 1B) Electron micrographs of U251 cells after 24 h treatment with MOPIPP show many large vacuoles (v), with some containing clusters of ILVs (asterisks). Scale bars=500 nm.

Treatment of cultured U251 glioblastoma cells with MOPIPP resulted in vacuolization of endocytic compartments. The accumulation of numerous vacuoles was readily detected by phase contrast microscopy (FIG. 1A). Treatment with vacuolin-1 induced a very similar phenotype (FIG. 1A). Despite the extreme vacuolization, the cells treated with both compounds remained attached to the culture dishes and continued to proliferate. Electron microcopy revealed that most of the vacuoles in the cells treated with MOPIPP were surrounded by a single membrane and were largely devoid of intralumenal contents (FIG. 1B). However, a distinct subpopulation of vacuoles (approximately 20-30%) contained clusters of heterogeneous vesicles, many of which were of a size (<50 nm) consistent with ILVs and exosomes (examples shown in FIG. 1B).

Figure 1C:
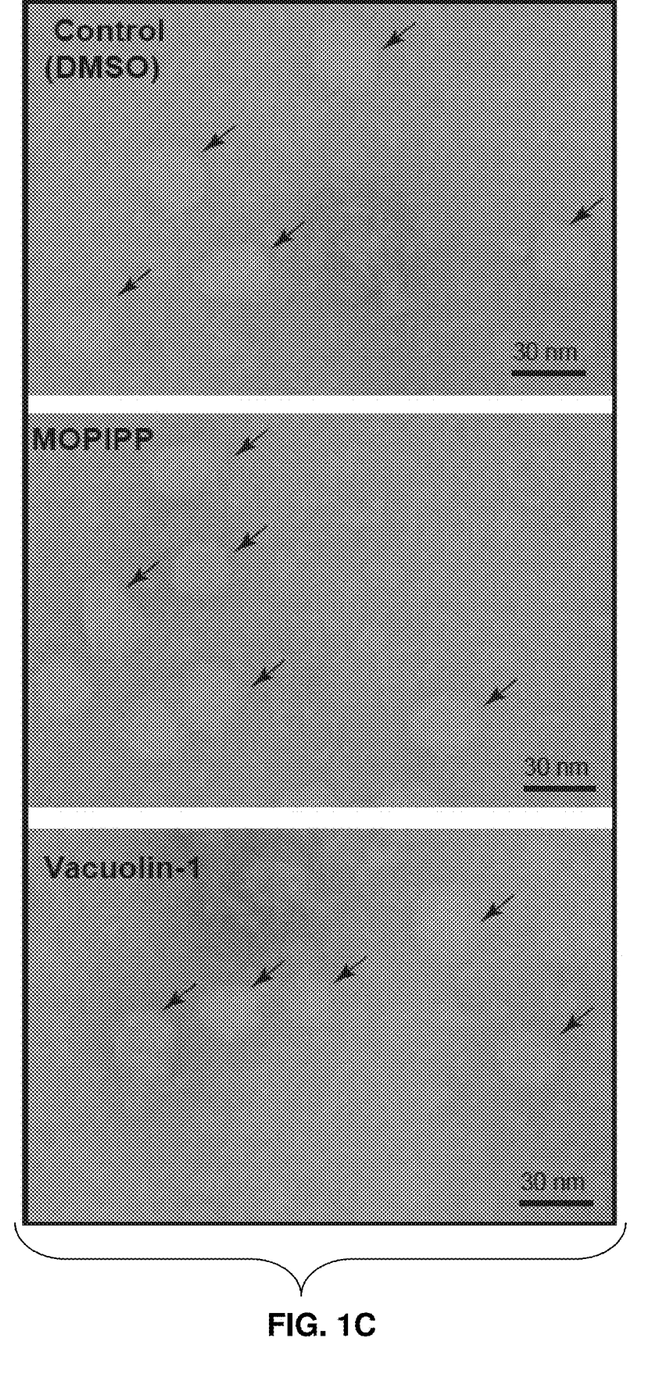
(FIG. 1C and FIG. 1D) Exosomes isolated from cells treated for 24 h with the indicated compounds were characterized by electron microscopy (FIG. 1C) or DLS (FIG. 1D).
Figure 1D:
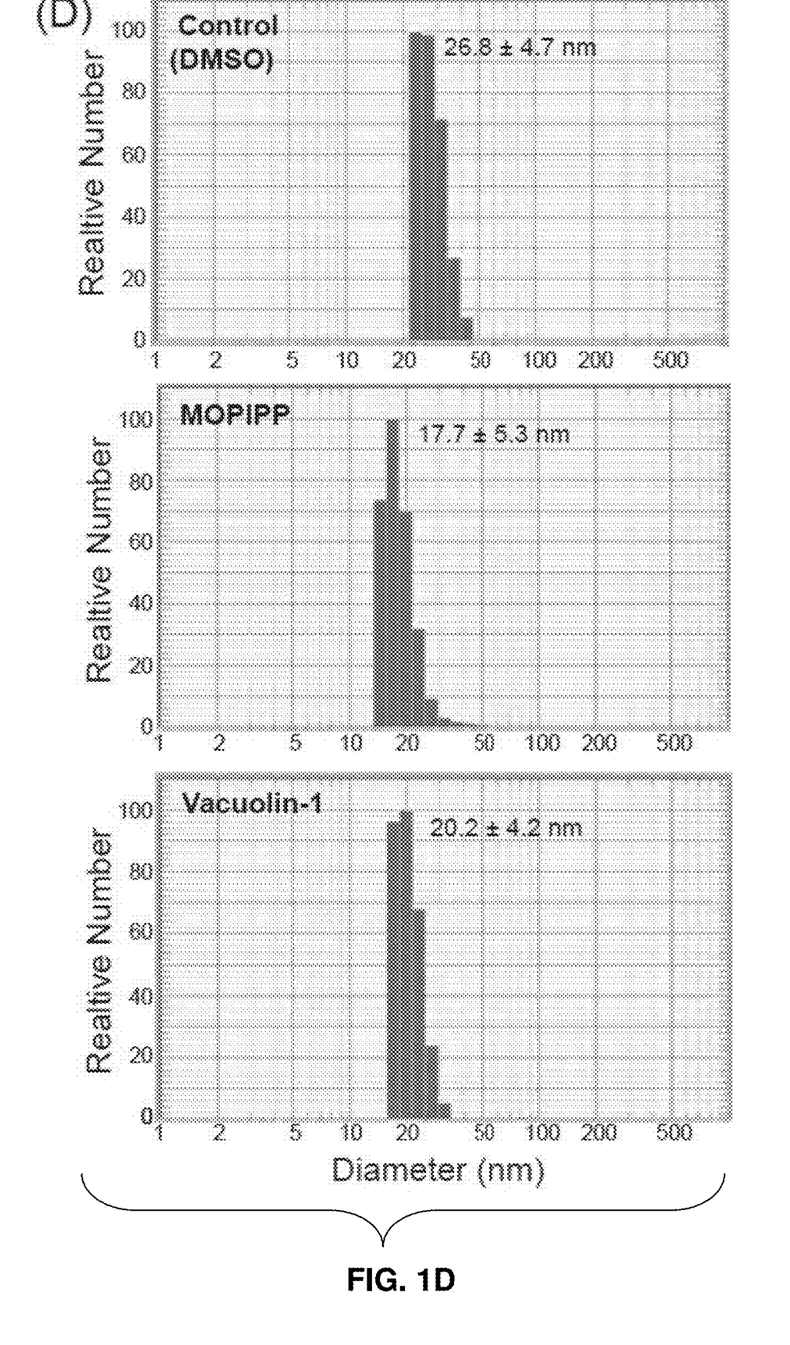

When 24-h conditioned media were collected from control and drug-treated cultures and subjected to a procedure designed to yield purified exosomes, electron microscopy showed that the final exosome fraction consisted mainly of vesicles with diameters of approximately 25-30 nm (FIG. 1C), matching the lower end of the size range reported for exosomes. There were no discernable differences in the morphologies of the vesicles obtained from the treated cells compared to the control. Particle analysis by DLS confirmed that the purified vesicle populations had unimodal distributions with mean diameters in the range of 18-27 nm. Differences between control and treated cells were not statistically significant (FIG. 1D).

Quantification of Exosome Marker Proteins

Figure 2A:
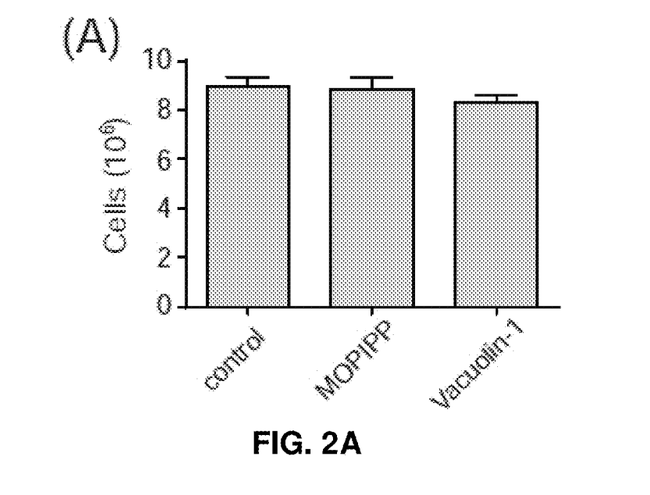
FIGS. 2A-2D—MOPIPP and vacuolin-1 increase the amounts of exosomal marker proteins in vesicle fractions recovered from conditioned medium. In three separate experiments, U251 cells were treated for 24 h with 10 μM MOPIPP, 1 μM vacuolin-1 or an equivalent volume of DMSO vehicle. The cells from each experiment were counted (mean±SEM) (FIG. 2A), and the medium from the same cultures was used to prepare exosomes with the Exo-Spin™ Purification method. Equal aliquots of the final exosome preparations were subjected to western blot analysis for the indicated proteins (FIG. 2B and FIG. 2C).
Figure 2B:
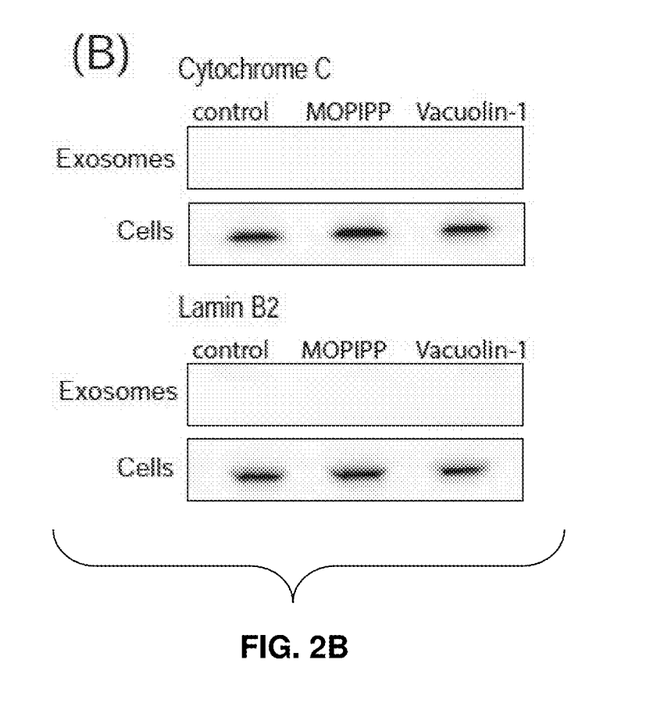
Figure 2C:
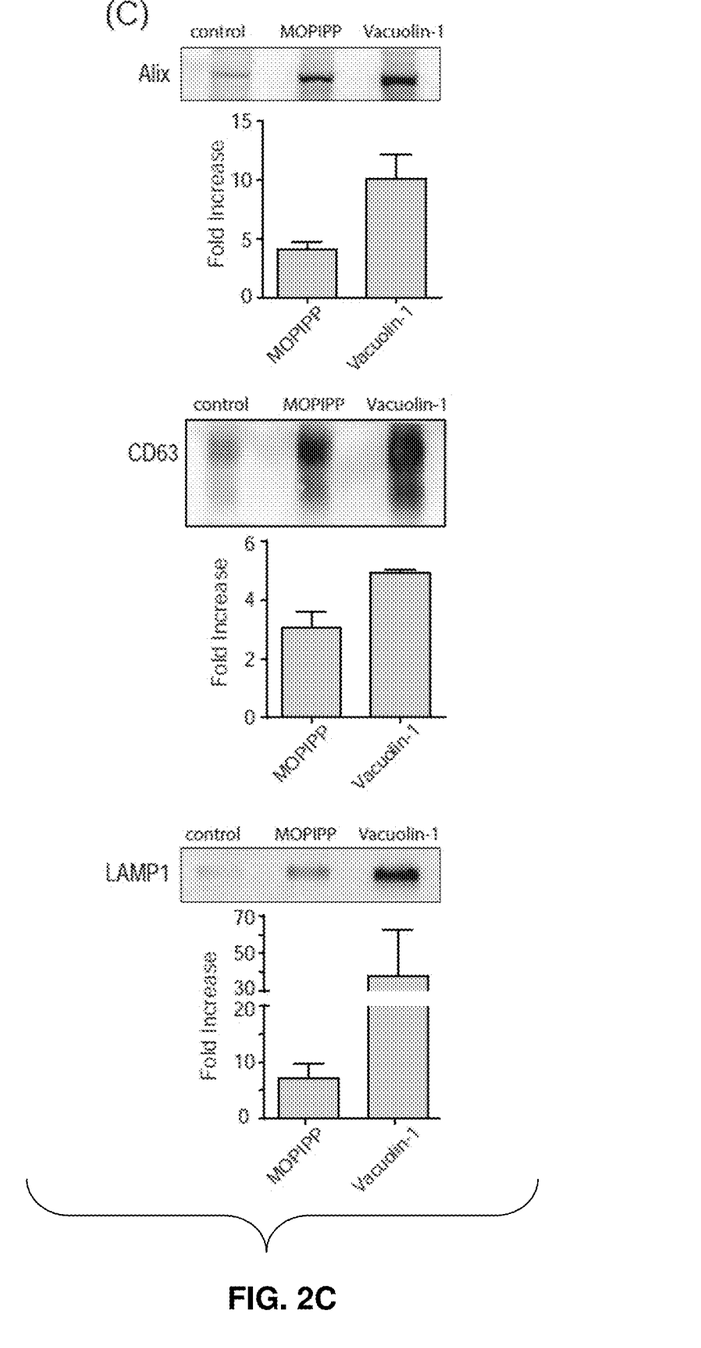
Figure 2D:
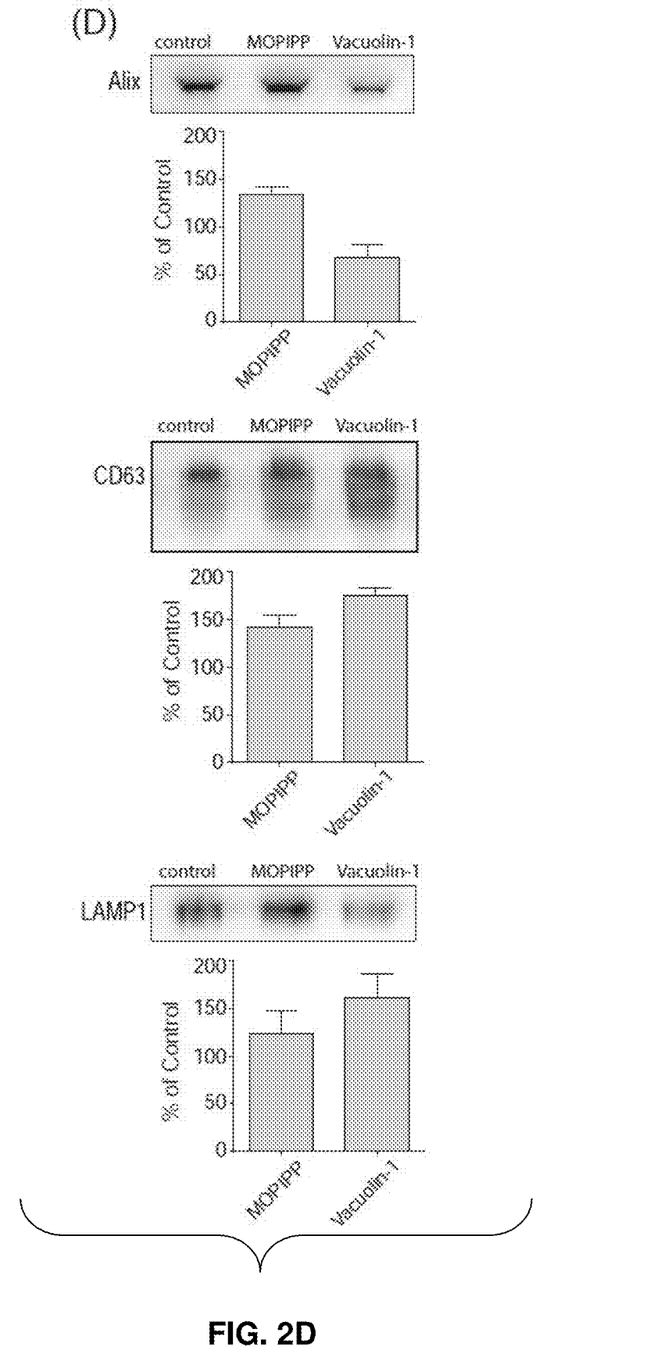

To determine if treatment with MOPIPP and/or vacuolin-1 might alter the production of exosomes, conditioned medium was pooled from 10-12 control or treated cultures and exosomes were isolated as described above. The cells from the same cultures were also harvested and pooled. FIG. 2A shows that comparable numbers of cells were present in the control and drug-treated cultures, consistent with the lack of growth inhibition by MOPIPP and vacuolin-1. The immunoblots in FIG. 2B demonstrate that cytochrome c and lamin $B_2$, markers for mitochondria and nuclear envelope respectively, were not detectable in the purified exosome populations, confirming that the latter were not contaminated with intracellular organelles released via cell lysis. In FIG. 2C and FIG. 2D, the isolated exosomes and cells were probed for three proteins commonly enriched in MVEs and exosomes: CD63, a member of tetraspanin protein family, Alix, a protein involved in the biogenesis of endosomal ILVs, and LAMP-1, an abundant membrane glycoprotein in lysosomes and late endosomes.

The results show that the relative amounts of all three proteins were increased by several fold in the extracellular vesicle preparations from cultures treated with MOPIPP (FIG. 2C). An even greater increase was observed in the cultures treated with vacuolin-1 (FIG. 2C). In contrast, changes in expression of the same marker proteins in the corresponding cell populations were comparatively modest (FIG. 2D). Since the exosomes were isolated from nearly identical numbers of cells in the control and treated cultures (FIG. 2A), the results show that MOPIPP and vacuolin-1 promote an increase in the release of exosomes into the extracellular environment.

Figure 3A:
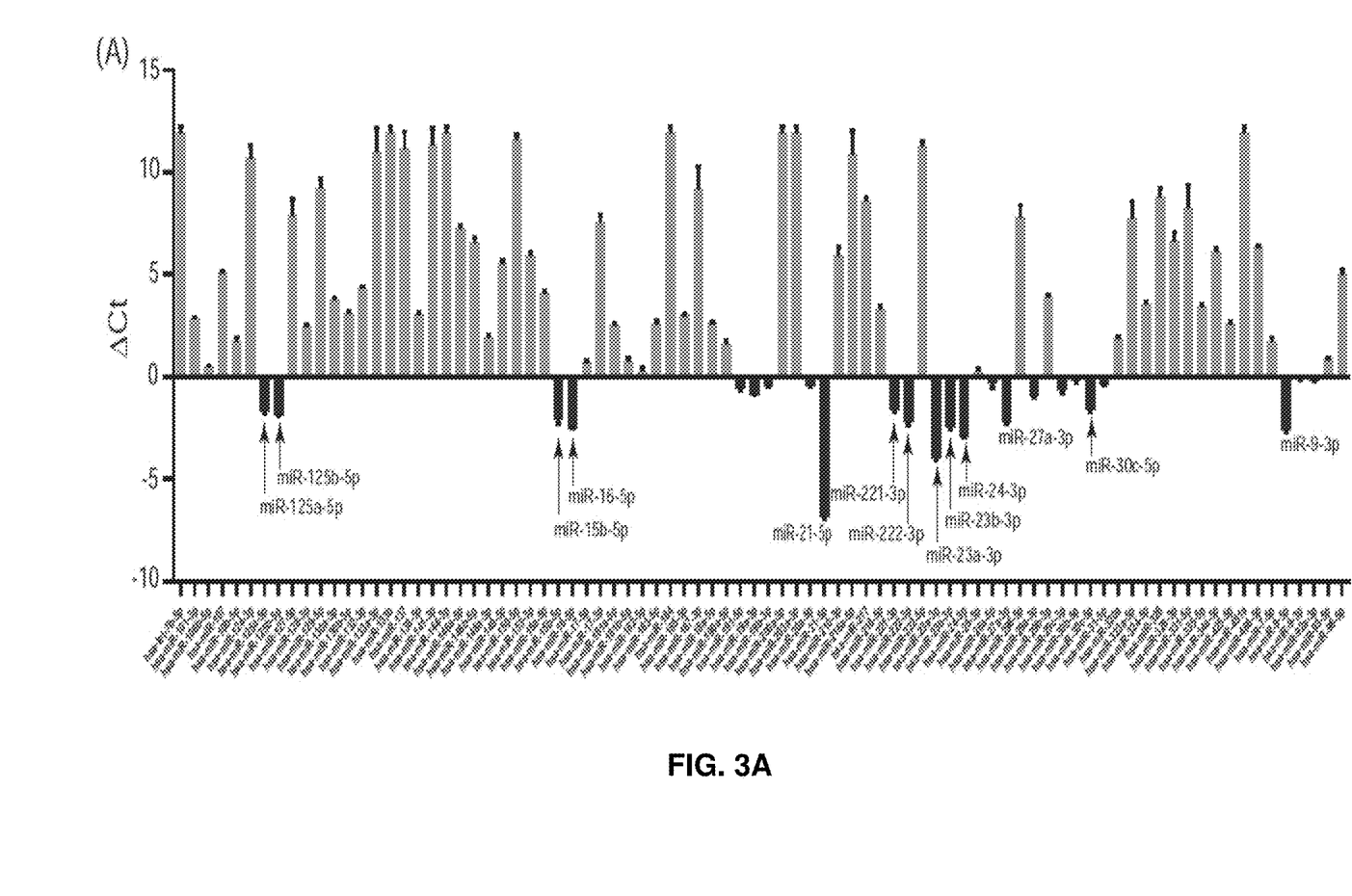
(FIG. 3A) Cellular miRNAs expressed in untreated U251 cells were profiled using the Human Brain Cancer miScript® arrays (n=3) and ΔCt values were determined using the six snoRNA/snRNA miScript PCR controls included on each array. The specific miRNAs selected for further study are indicted with arrows.

Comparison of miRNA Profiles miRNA cargoes carried by exosomes play important roles in intercellular communication. As shown herein, it was then determined whether, in addition to increasing exosome output, MOPIPP and vacuolin-1 would alter the miRNA composition of the exosomes. miRNAs expressed in untreated U251 glioblastoma cells were profiled, using a RT-PCR array that detects 84 miRNAs commonly associated with human brain cancers. Based on their ΔCt values relative to a panel of six normalization controls (FIG. 3A), 13 miRNAs with high expression were selected for further comparison between control and MOPIPP-treated cells.

Figure 3B:
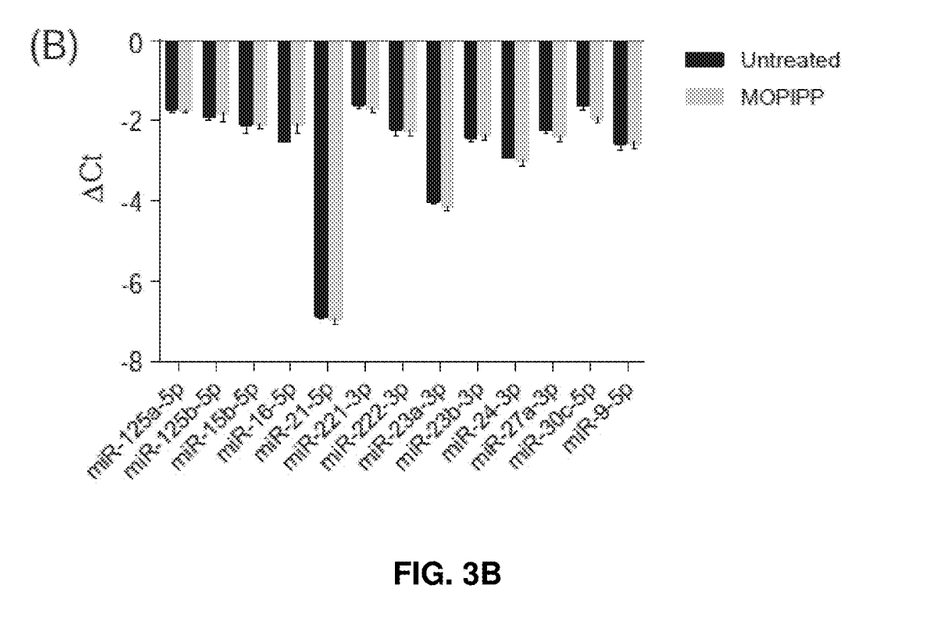
(FIG. 3B) U251 cells were treated with 10 μM MOPIPP or an equivalent volume of DMSO for 24 h and cellular expression of each of the indicated miRNAs was determined by RT-PCR (n=3).
Figure 3C:
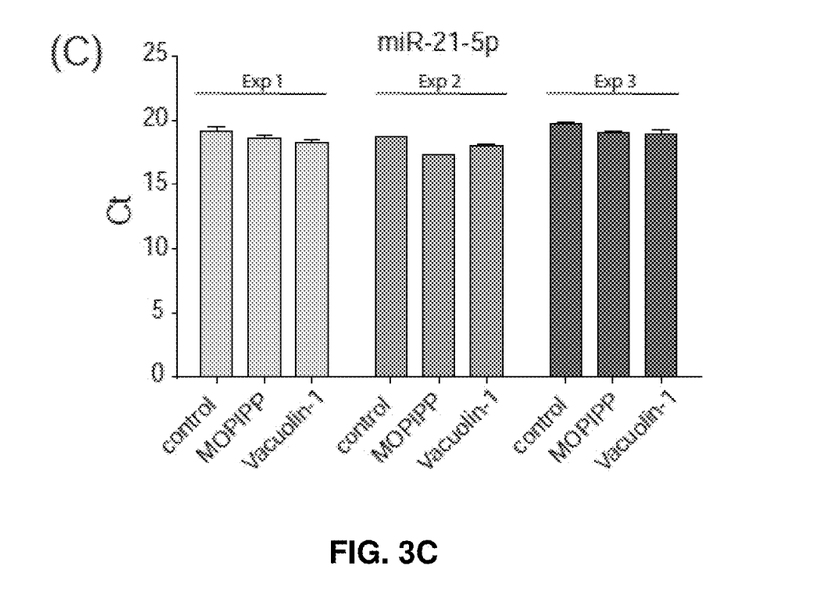
(FIG. 3C) In three separate experiments, exosomes were isolated from U251 cells treated with MOPIPP, vacuolin-1 or DMSO and equal amounts of exosomal RNA were subjected to reverse transcription and RT-PCR to assess miR-21-5p.

As shown in FIG. 3B, treatment with MOPIPP did not cause major changes in the cellular expression of any of the selected miRNAs. Among the miRNAs profiled on the array, miR-21-5p was clearly the most abundant. RT-PCR reactions were carried out with miR-21-5p primers to assess the relative amounts of miR-21-5p in exosomes collected from cells treated with MOPIPP or vacuolin-1, compared to untreated controls. Since the selection of a definitive RT-PCR standard for normalization of exosomal miRNA is controversial, triplicate reactions were set up with equal amounts of total exosomal RNA from control and treated cells and directly compared the raw Ct values (FIG. 3C).

Figure 3D:
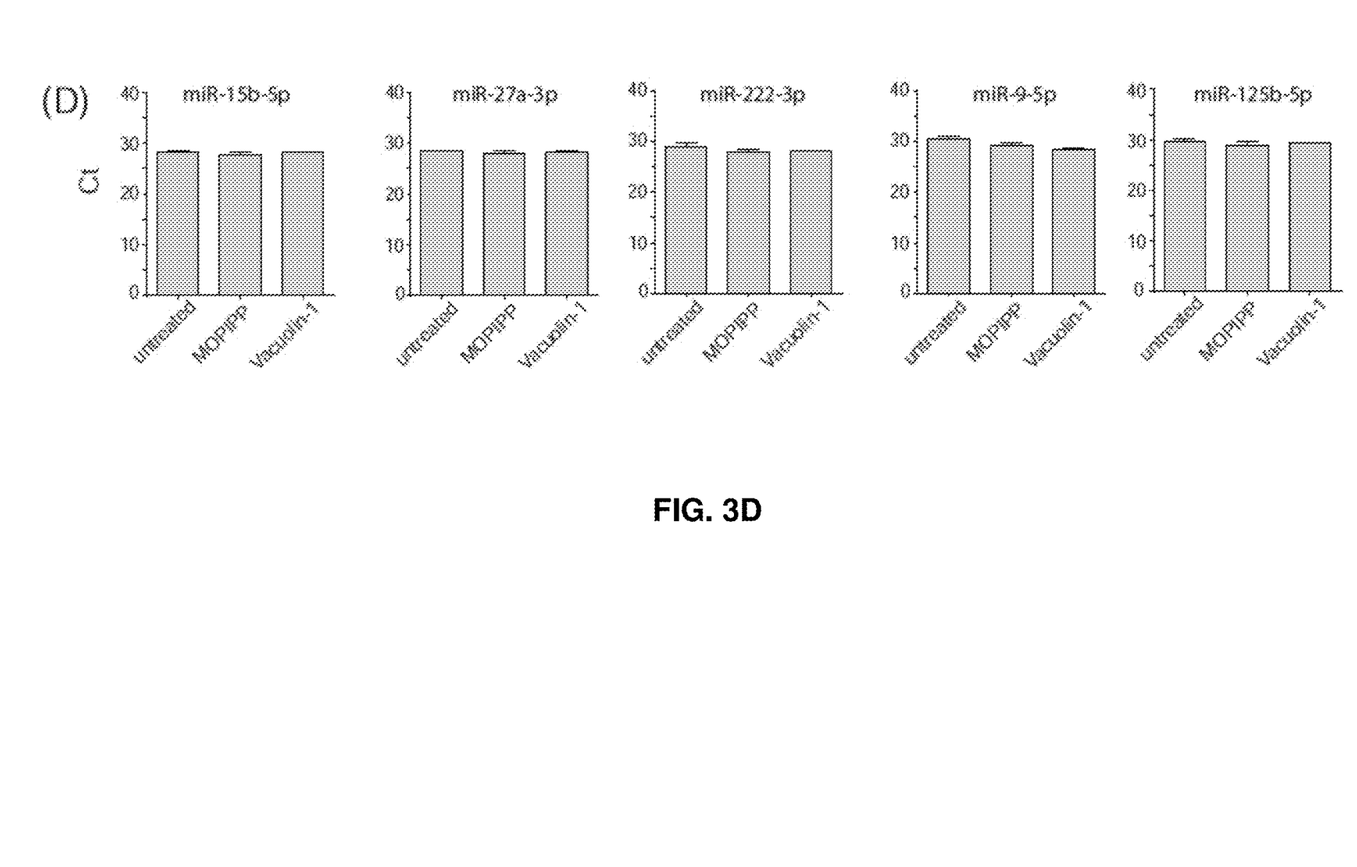
(FIG. 3D) RT-PCR comparisons of five additional miRNAs, starting with equal amounts of exosomal RNA from cells treated with MOPIPP, vacuolin-1 or DMSO.

Using this approach for three independent experiments, there were no observations of any changes in the relative abundance of miR-21-5-p in exosomal RNA collected from cells treated with MOPIPP or vacuolin-1. Similar results were obtained when the analysis was extended to five additional miRNAs (FIG. 3D).

Discussion

The results show that vacuolization of late endosomal compartments induced by two distinct small molecules, MOPIPP and vacuolin-1, is accompanied by a several-fold increase in exosomal marker proteins in extracellular vesicles prepared from comparable numbers of glioblastoma cells. Cell proliferation and viability were not markedly impaired by these compounds, and the characteristics of the exosomes from treated cells were similar to the controls. Since the intracellular amounts of the marker proteins were only modestly affected by the compounds, the results are indicative of an increase in exosome biogenesis and/or secretion in cells treated with MOPIPP and vacuolin-1.

Small molecules that promote vacuolization of late endosomal compartments have the potential to affect exosome production in several ways. In one scenario, vacuolization of endosomes could disrupt the molecular machinery for the formation of ILVs, so that any MVEs that subsequently fuse with the plasma membrane release fewer exosomes. In a second scenario, formation of ILVs might remain unaffected, but trafficking of enlarged MVEs to the cell surface might be disrupted, also resulting in diminished exosome secretion. Finally, in a third scenario, drug-induced vacuoles derived from late endosomes could retain the ability to generate ILVs, but be unable to merge with lysosomes where the vesicles are degraded. In that case, enlarged MVEs might accumulate and deliver more ILVs to the extracellular environment, provided that they remain competent to fuse with the plasma membrane. It is now believed that the third scenario explains the increase in exosome secretion (FIG. 2), considering that many vacuoles in MOPIPP-treated cells contained numerous ILVs (FIG. 1B).

The miRNA cargo carried by exosomes may differ from the miRNA profile of the producer cell, implying that segregation of miRNAs into exosomes is not random. It is now shown herein that extensive vacuolization of endosomal compartments did not affect the expression of several common miRNAs in glioblastoma cells. Furthermore, the vacuole-inducing compounds did not substantially alter the relative concentrations of several miRNAs represented in the total RNA in the secreted exosomes. Thus, while the analysis of exosomal proteins shows that MOPIPP and vacuolin-1 induce large increases in exosome secretion, the exosomes appear to be qualitatively similar to those collected from untreated cells in terms of their miRNA cargo.

Therapeutic Uses

As described herein, inventive vacuole-inducing molecules induce vacuolization in cells without cell death. In this regard, the present vacuole-inducing molecules are useful in a number of pathological applications. Certain applications are mentioned below; others will be apparent to those of ordinary skill in the art.

Therefore, vacuole-inducing molecules can be used to induce vacuolization without cell death of cancer cells. For example, the present are useful in treating cancers of the brain, lung, bladder, liver, spleen, pancreas, bone, colon, stomach, breast, prostate, ovary, central nervous system and skin. For example, glioblastoma and breast carcinoma can be treated.

Further non-limiting examples of therapeutic applications of exosomes include using these vesicles as nanocarriers for packaging and delivery of small molecules (e.g., anti-cancer drugs), miRNAs, and proteins.

Small molecules like MOPIPP are useful as non-cytotoxic pharmacological agents to boost exosome production.

Research Uses

In addition to the various pharmaceutical uses described above, vacuole-inducing compounds have utility in a variety of research applications, e.g., in vitro assays, including, for example, as chemical probes. Those of ordinary skill in the art will appreciate that the field of chemical genetics attempts to identify chemical agents with definable effects on biological events, pathways, or products so that these agents can be used as tools to analyze the relevant biological events, pathways, or products. Vacuole-inducing molecules described herein are particularly well suited for such studies. Accordingly, such uses also include assays, e.g., in vitro assays, utilizing the vacuole-inducing molecules to analyze vacuolization, intracellular trafficking, antigen presentation, membrane fusion events, and related cellular processes. Furthermore, the vacuole-inducing molecules can also be used in screening assays to identify second generation vacuole-inducing molecules, e.g., molecules having modified chemical structures which function as vacuole-inducing molecules. Azide, propargyl or other forms of the vacuole-inducing molecules can be used in a variety of cell-based or molecular screening assays to identify specific protein targets that bind to such molecules.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

The publication and other material used herein to illuminate the invention or provide additional details respecting the practice of the invention, are incorporated by reference herein, and for convenience are provided in the following bibliography.

Citation of any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

What is claimed is:

1. A method for increasing exosome production in cells in a cell culture, comprising:
   i) exposing the cell culture to a non-cytotoxic dose of an indole-pyridinyl-propenone compound sufficient to keep the cells in the cell culture alive and producing exosomes, wherein the compound has the following chemical structure:

R=OH, $OCH_3$, $OCH_2CH_3$, $OCH(CH_3)_2$, $NHCOCH_3$ or $NHCO_2C(CH_3)_3$; and
R'=H, $CH_3$, $CH_2CH_2CH_3$, $CH(CH_3)_2$, or $CH_2CH(CH_3)_2$, excluding the compound where R=$OCH_3$ and R'=$CH_3$;
   ii) inducing exosome production by the cells in the cell culture, without triggering growth arrest or cell death and;
   iii) collecting exosomes produced by the cells in the cell culture.

2. The method of claim 1, wherein R=$OCH_3$; and, R'=H, $CH_2CH_2CH_3$, $CH(CH_3)_2$, or $CH_2CH(CH_3)_2$.

3. The method of claim 2, wherein R=$OCH_3$, and R'=$CH_2CH_2CH_3$.

4. The method of claim 1, wherein R=OH, $OCH_2CH_3$, $OCH(CH_3)_2$, $NHCOCH_3$ or $NHCO_2C(CH_3)_3$; and, R'=$CH_3$.

5. The method of claim 4, wherein R=$OCH_2CH_3$; and, R'=$CH_3$.

6. The method of claim 1, wherein R=$OCH_2CH_3$; and R'=$CH_2CH_2CH_3$.

7. The method of claim 1, wherein collecting exosomes is conducted by one or more of the following: ultracentrifugation; column chromatography; size exclusion; and filtration through a device containing an affinity matrix that is selective toward exosomes.

8. The method of claim 1, wherein the cell culture comprises one or more of: multipotent mesenchymal stromal cells; stem cells; and, cancer cells.

9. The method of claim 1, wherein the cell culture is a mammalian cell culture.

* * * * *